US005580749A

United States Patent [19]

Hughes

[11] Patent Number: 5,580,749
[45] Date of Patent: Dec. 3, 1996

[54] INTERNAL REFERENCE FOR CHEMICALLY MODIFIED SPHERES

[75] Inventor: Kenneth D. Hughes, Marietta, Ga.

[73] Assignee: Georgia Tech Research Corporation, Atlanta, Ga.

[21] Appl. No.: 327,286

[22] Filed: Oct. 21, 1994

[51] Int. Cl.$^6$ ............... C12Q 1/02; C12Q 1/22; C12Q 1/37; G01N 33/551
[52] U.S. Cl. ............... 435/29; 435/31; 435/24; 435/23; 435/18; 435/34; 435/4; 436/63; 436/172; 436/800; 436/524; 436/527
[58] Field of Search ............... 435/29, 18, 4, 435/31, 24, 23, 34; 436/63, 172, 800, 524, 527

[56] References Cited

U.S. PATENT DOCUMENTS

| | | | |
|---|---|---|---|
| 3,633,546 | 1/1972 | Guttag | 435/29 |
| 4,035,316 | 7/1977 | Yen | 260/2.5 B |
| 4,438,239 | 3/1984 | Rembaum | 525/54.1 |
| 4,467,035 | 8/1984 | Harasawa et al. | 435/29 |
| 4,784,912 | 11/1988 | Schaeffer | 428/402 |
| 4,801,504 | 1/1989 | Burdick | 428/403 |
| 4,891,324 | 1/1990 | Pease | 436/519 |
| 5,094,944 | 3/1992 | Hayes et al. | 435/29 |
| 5,132,242 | 7/1992 | Cheung | 436/501 |
| 5,135,746 | 8/1992 | Matsuno et al. | 435/29 |
| 5,194,300 | 3/1993 | Cheung | 427/213.31 |
| 5,273,768 | 12/1993 | Earle et al. | 435/29 |

OTHER PUBLICATIONS

Bronk et al, "Analy Biochem", vol. 210, pp. 219–225 (1993).
Ohkusa et al, "J. Biochem", vol. 109 (4), Abstract, (1991) p. 609.
O'Connor et al, "In Vitro Toxicol.", vol. 4(3), Abstract, (1991), p. 197.
"Dynamic Measurements of Intracellular Aminopeptidase Activity in Hepatocytes Using Multiparameter Digitized Video Fluorescent Microscopy", Anal. Biochem., 210, pp. 219–225 (1993) By Bronk et al.

Primary Examiner—John Kight
Assistant Examiner—Louise N. Leary
Attorney, Agent, or Firm—Oldham & Oldham Co. L.P.A.

[57] ABSTRACT

A probe system for monitoring chemical activity of a target chemical in an environment has first and second marker compounds each bonded to a common substrate to keep the respective markers in physical proximity. The first marker is a chemical that has a maximum emission intensity at a first wavelength, and it is chemically shielded from the environment being studied. The second marker is a chemical that, when in a first state, has a maximum emission intensity at a second wavelength different from the first wavelength and which, in a second state, does not have a maximum emission intensity at the second wavelength. The second marker is convertible between said states through chemical reaction with the target chemical. The common substrate is a carrier particle, the first marker being impregnated within the carrier particle and the second marker being chemically bonded to the exterior surface of the carrier particle. The carrier particle may be a polymeric material, such as polystyrene, especially formed into a microsphere. The second marker may be in the second state prior to chemical reaction with the target chemical and is converted to the first state after chemical reaction with the target chemical, or it may be in the first state prior to chemical reaction with the target chemical, convertible to the second state by the chemical reaction with the target chemical.

22 Claims, 2 Drawing Sheets

INTERNAL REFERENCE FOR CHEMICALLY MODIFIED SPHERES

The present invention relates to a probe system for monitoring chemical activity of a target chemical where the probe system has first and second markers, the first marker being a fluorescent compound and the second marker being a compound capable of fluorescing at a wavelength different from the first marker, the first and second markers being physically attached to a common substrate, assuring that the first and second markers remain in spatial proximity. More particularly, the first marker compound is impregnated into a carrier particle, particularly a polymeric particle, and a second marker compound is chemically attached to the surface of the particle. In a chemical system, particularly a biological system, the first marker compound is a chemical that is completely shielded from the chemical system by the impregnation and that will emit with a maximum intensity at a first wavelength when irradiated at a given wavelength. The second marker compound is a covalently-bonded substrate compound that will change its emission intensity, which has a maximum at a second wavelength, different from the first wavelength, when the second marker compound is chemically cleaved by the target chemical. The emission change effected by the cleavage could be either an increase or decrease in the emission intensity at the second wavelength. More particularly, the first and second markers are compounds that will fluoresce when stimulated with electromagnetic radiation, particularly in the visible spectrum. In some specific applications, a polymer chain such as a poly(amino acid), may be used to provide a plurality of attachment sites for the second marker for each attachment site on the particle surface.

BACKGROUND ART

It is becoming increasingly valuable to be able to measure enzymatic activity in living organisms. Since enzymes mediate all major cellular functions, such as metabolism, respiration and immune system response, analysis of enzymatic activity plays an important role in understanding cellular function, and diagnosing and treating disease.

Fluorescence-based analytical methods provide a sensitive means to investigate cellular enzymatic activity. These techniques are especially amenable to recently-developed microscopic imaging technologies which allow two-dimensional images to be collected, analyzed with computer software and stored in a digital format. The research in this arena focuses on the spatial and temporal characteristics of enzymatic activity in single cells and single microorganisms. Investigations of single cells and single microorganisms allows better understanding of the bulk data collected when analyzing populations of cells or organisms. Even further, the real possibility of identifying cells or organisms possessing specific characteristics, desired or undesired, will prove to be useful in medicine, chemistry and environmental research.

In some prior work by Bronk, Powers and Gores at the Mayo Medical School and reported in the journal *Analytical Biochemistry*, Vol. 210, pp. 219–25 (1993), a baseline emitter was chemically attached to a first carrier particle and the active component was chemically attached to a second carrier particle. In this work the baseline emitter was rhodamine, which was attached to the first carrier particles, made of dextran. The active component was glycine-7-amino-4-methylcoumarin-3-acetic acid ("glycine-AMC-3-acetic acid"), a non-fluorescer, which was attached to the second carrier particles, also dextran, by a polyethylene glycol ("PEG") bridge. A mixture of the two types of carrier particles was microinjected into cultured rat hepatocytes to measure aminopeptidase activity. When the active component particles are exposed to the hepatocyte environment, the attack of the aminopeptidase upon the glycine attachment to the glycine-AMC-3-acetic acid-PEG-dextran liberates the fluorescent compound AMC-3-acetic acid-PEG-dextran. The emission intensity of rhodamine-dextran remained constant over time, but the emission intensity of AMC-3-acetic acid-PEG-dextran increased in a linear fashion, indicating the proteolytic cleavage of the glycine-AMC bond. The measurement of the emission intensity was achieved through the known technique of single excitation dual emission wavelength ratio technique ("SEDERT"). As it turned out, the first and second carrier particles co-localized in the cytosol, that is, the cytoplasm of the cell less the mitochondria and endoplasmic reticulum components, as indicated by the diffuse fluorescence of each across the cytosol. This allowed the fluorescent ratio of the active component to the baseline emitter to be compared, thus measuring proteolysis. However, had the first and second carrier particles not co-localized, the ratio technique would not have been possible.

In the field of fluorescence-based biological assays, several difficulties are encountered, but the major difficulty involves delivery of the fluorescent probe to the targeted location. It is well known to use acetoxymethyl esters to transport fluorescent ion and enzyme probes through the cell membrane, but these systems often require use of dimethylsulfoxide ("DMSO") as the carrier-reagent. Once through the membrane, the intercellular esterases transform the probe into an active state. However, not all probes are amenable to this type of derivatization, and long incubation times are often required to deliver a measurable amount across the membrane. Once inside the cell, unwanted localization or undesirable binding of the fluorescent probe is common. This localization may be due to a variety of factors, including solubility and electrical potential characteristics of the probe relative to membranes and cell organelles. Similarly, non-uniformities in the source intensity of the excitation source result in fluctuations in the measured fluorescence, and detract from quantitation of the cellular processes. Without a baseline against which to compare the active probe intensity, these fluctuations impose huge obstacles to an otherwise convenient test method.

SUMMARY OF THE INVENTION

It is therefore, a first object of the present invention to provide an indicating probe for assay work wherein a first and a second marker compound are kept in a fixed spatial arrangement so that the first marker compound, which is positioned so as to be shielded from the environment, provides a baseline maximum emission intensity at a first wavelength and the second marker compound, which is exposed to the environment, provides a maximum emission intensity at a second wavelength either before or after chemical cleavage of the second marker compound by a target chemical present in the environment in a manner that does not require co-localization of two separate particles in the environment.

This and other objects are achieved by a probe system for monitoring chemical activity of a target chemical in an environment. The probe system comprises a first marker and a second marker, each bonded to a common substrate to keep the respective markers in physical proximity. The first marker is a chemical having a maximum emission intensity at a first wavelength. This first marker is chemically shielded from the environment containing the target chemical. The second marker is a chemical that, when in a first state, has a maximum emission intensity at a second wavelength different from the first wavelength and which, in a second state, does not have a maximum emission intensity at the second wavelength. The second marker is convertible between said states through chemically reaction with the target chemical. In a particular embodiment, the common substrate is a carrier particle, the first marker being impregnated within the carrier particle and the second marker being chemically bonded to the exterior surface of the carrier particle. The preferred carrier particle is comprised of a polymeric material, especially polystyrene. The preferred carrier particle shape is a microsphere having a diameter in the range of 0.01 to 50 microns in diameter. In another embodiment, the carrier particle is composed of a material that itself acts as the first marker, such as a glass that exhibits luminescent properties. In some embodiments, the second marker is in the second state prior to chemical reaction with the target chemical and is in the first state after chemical reaction with the target chemical. An example of this would be a compound such as fluorescein diacetate, which is non-fluorescing, but which is chemically cleavable to yield the highly fluorescent fluorescein. In other embodiments, the second marker is in the first state prior to chemical reaction with the target chemical and is in the second state after chemical reaction with the target chemical. In some further embodiments, the second marker comprises a polymeric composition having a backbone structure with a plurality of molecules grafted onto the backbone structure along the length thereof, wherein said grafted molecules, when in a first state, have a maximum emission intensity at a second wavelength different from the first wavelength and which, in a second state, do not have a maximum emission intensity at the second wavelength, said grafted molecules being convertible between said states through chemically reaction with the target chemical. In a particular example, the backbone structure is a poly(amino acid), such as a poly(lysine) chain, especially one having an average molecular weight in the range of 4,000 to 10,000 amu, and the plurality of grafted molecules are molecules of 5,6 carboxyfluorescein diacetate.

The invention also covers a method for measuring chemical activity of a target chemical in an environment. This method comprises the steps of adding a probe system to the environment and measuring the change in an emission intensity ratio with time, where the probe system is the probe system described above and the emission intensity ratio is the emission intensity of an emission maximum wavelength of the second marker divided by the emission intensity of an emission maximum wavelength of the first marker. Such a measure may be achieved through digitized video fluorescent microscopy.

A specific application of the method and probe of the present invention is found in measuring environmental stress in an aquatic organism by adding a probe system to an aquatic system containing a plurality of the aquatic organisms, monitoring uptake of the probe system by the aquatic organism; and measuring the change in emission intensity ratio with time in the digestive tract of the aquatic organism.

BRIEF DESCRIPTION OF THE DRAWINGS

A more complete understanding of the present invention will be obtained when reference is made to the following detailed description of the preferred embodiment, and the accompanying figures, wherein:

FIG. 2 shows a plot of relative intensity v. wavelength for a marker system as taught in Example 2; and.

DETAILED DESCRIPTION OF THE PREFERRED EMBODIMENT

Figure 1:
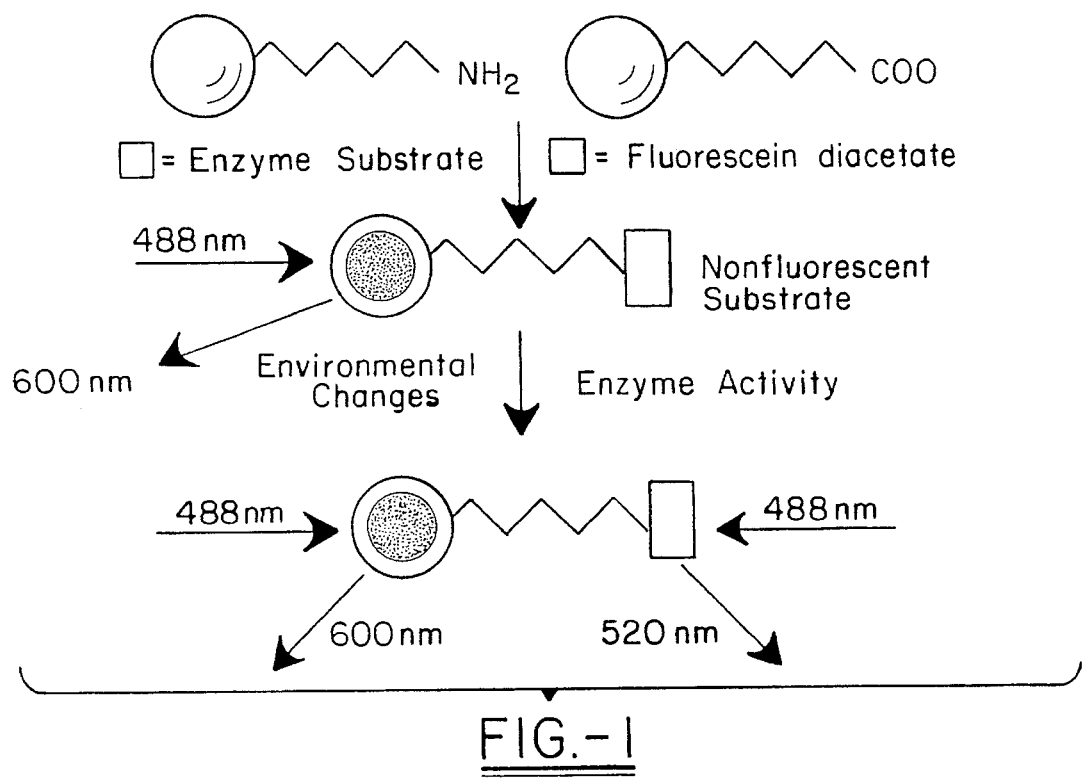
FIG. 1 shows a schematic diagram of the probe system of the present invention.

The present invention involves the preparation of a unique probe system intended to monitor chemical activity of a target chemical in a specific environment, particularly a microenvironment, as may be observed around or in a microorganism. The probe system, which is shown schematically in FIG. 1, comprises a carrier particle with first and second markers. As is explained further below, the first marker is a chemical that has a maximum emission intensity at a first wavelength. The second marker is a chemical that, when in a first state, has a maximum emission intensity at a second wavelength different from the first wavelength and which, in a second state, does not have a maximum emission intensity at the second wavelength. The transformation of the second marker between the first and second state is accomplished through a chemical reaction between the second marker and the target chemical. In the preferred method of practicing the invention, the first marker is impregnated within the carrier particle, resulting in it being chemically shielded from the environment. In this manner, the first marker is rendered chemically inert in the environment and will provide a constant baseline emission intensity at a selected wavelength. The second marker is chemically bonded to the exterior surface of the carrier particle as described further below. The second marker, being chemically exposed to the environment containing the target chemical, is chemically convertible from one state to the other by reaction with the target chemical. In some systems of interest, the target chemical will be of biological origin, such as an enzyme. In other systems of interest, the target chemical will be of non-biological origin, such as an acid or a base. In a preferred embodiment of this invention, the environment is the interior of a living organism. In other embodiments, the specific environment being studied may be a general environment containing the target chemical. For practical purposes, the preferred environment will be the liquid phase, and an aqueous liquid phase is most preferred.

The Probe Particle

The probe particle used in the invention is known in the prior art and is commercially available. The preferred particle is a spherical particle, for the obvious advantage of high surface area to volume ratio, which becomes useful in attaching the external marker to the particle. However, there may be instances where other geometries may be desirable. The preferred particle is substantially solid, but bubbles or other voids may be entrained in the particle during manufacture to adjust the overall density, if necessary. This will often be desirable to provide a particle that is substantially the same density as that of the work environment and will remain dispersed within it, to prevent the particles from either sinking to the bottom or floating to the top of the system The preferred probe particle size will be determined by the service for which it is intended, but the typical particles used will have a diameter of at least about 0.01 µm and will not generally exceed a diameter of about 50 µm. In biological applications, the larger size limit will be set practically by the mobility the particle needs and the ability of the organism to ingest the probe, and the smaller size limit will effectively be set by the ability to reliably make and manipulate the probe particle.

Latex spheres made of an organic polymer such as polystyrene but not containing the first marker are commercially marketed by companies such as Dow Chemical Company and Polysciences, Inc., as well as others.

The First Marker

The first marker compound of the present invention will be dispersed with the probe particle, so it must be compatible with the probe particle. In one method of impregnating the probe particles, an aliquot of the first marker is added to a melt of polymeric material from which the probe particles are formed by known techniques. In a second method, particularly useful when a glass is used as the probe particle, the inherent luminescence of the glass composition when exposed to radiation of a specific wavelength effectively allows the particle itself to act as the first marker. An example of this is presented below. In any case, the first marker must be chosen so that the maximum emission wavelength is sufficiently distant from the maximum emission wavelength of the second marker that the two emissions are distinguishable when observed. To assure that the first marker provides a reliable baseline emission, the first marker should be selected so that it is completely shielded chemically from the environment and is not subject to be leached from the particle.

The Second Marker

The second marker compound of the present invention is determined by a variety of factors. First among these is the capacity of the second marker compound to have a first (emitting) state and a second (non-emitting) state, the difference between the states being a chemical reaction with a target chemical. For example, the first state could be the fluorescing compound fluorescein, and the second state could be the non-fluorescing compound fluorescein diacetate. The conversion between the second state and the first state can be effected by reaction of the fluorescein diacetate with a target chemical, such as the digestive enzyme esterase. In this case, the emission intensity is "turned on" by the chemical reaction. In another situation, it might be desirable to convert an emitting compound into a non-emitting compound through the chemical reaction. An example of this is would be the reaction of the emitting compound with a target chemical to give a non-emitting compound. In this latter situation, the emission intensity is "turned off" by the reaction. One such example would be with the same fluorescein molecule, which is certainly susceptible to degradation to non-fluorescing species. Such degradation would be expected to occur due to oxidation, for example.

A second factor in the selection of the second marker is the ability to covalently bond the marker to the probe particle such that the bonding site is not subject to chemical attack by the target chemical. If the marker cannot be bonded firmly to the particle, there can be no assurance that there will be a proximal association of the first and second markers, which is essential to the use of the first marker emission as a baseline. However, this factor is ameliorated substantially if the second marker can be covalently bonded to a "bridge" compound, such as a poly(amino acid) or dextran, which can be covalently bonded to the particle.

A third factor is to select a second marker that is able to covalently bond to the particle at a site on the second marker that does not impede the ability of the second marker to be converted between the emitting and non-emitting state and also not impede the ability of the second marker to emit when in the first state.

EXAMPLE 1

Solid 5,6 carboxyfluorescein diacetate succinimidyl ester ("CFSE") was obtained from Molecular Probes, Inc., of Eugene, Oreg., and stored at 0° C. DMSO was obtained from Baker. Microparticles containing fluorescent dye in the particles were also obtained from Molecular Probes, Inc., or Interfacial Dynamics Inc. The particles were in the 0.933 micron range. The microparticle spheres are manufactured by Interfacial and have amine functional groups (six carbon extensions) and are impregnated by Molecular Probes with various fluorophores, such as Nile Red. Such microspheres are sold by Molecular Probes under the tradename FLUOSPHERES—NILE RED.

One milligram of the CFSE in DMSO was placed in a vial containing 0.5 ml of the microspheres, with a concentration of approximately $1 \times 10^{10}$ particles/ml). After three hours of incubation at a temperature of about 25° C., conjugation of the carboxyfluorescein diacetate marker to the particles was obtained by formation of an amide bond between the marker and the particles. Excess marker compound was cleaned up by dialysis against DMSO. Particles marked in this manner with the Nile Red and the carboxyfluorescein diacetate marker were refrigerated (frozen) in the DMSO until used.

EXAMPLE 2

Solid 7-amino-4-methylcoumarin acetic acid succinimidyl ester ("AMC-acetic acid succinimidyl ester") was obtained from Molecular Probes, Inc., of Eugene, Oreg., and stored at 0° C. Solid t-butyl carbonyl-alanine ("T-BOC-alanine") was obtained from Sigma Chemical Co. and also stored at 0° C. Dye impregnated microparticles identical to those used in Example 1 were obtained. Ethyl acetate, ethyl chloroformate and dimethylformamide ("DMF") were obtained from Baker. Controlled Pore Glass (amine functionalized, 400 mesh) was obtained from Sigma Chemical and stored dry.

A solution having 10 mg of the AMC-acetic acid succinimidyl ester per ml of DMF was reacted with 0.5 ml of the microspheres, with a concentration of approximately $1 \times 10^{10}$ particles/ml). After four hours of incubation at a temperature of about 25° C., conjugation of the 7-amino-methylcoumarin marker to the particles was obtained by formation of an amide bond between the marker and the particles. Excess marker compound was cleaned up by dialysis against DMF. Then, 5.5 mg of the T-BOC-alanine and 3.5 µl of N-methyl morpholine was dissolved in 100 µl of ethyl acetate. The solution was cooled to −14° C. and ethyl chloroformate added dropwise to form the mixed anhydride. This anhydride solution was then added dropwise to the marked spheres. After ten minutes, the reaction mixture was allowed to warm to room temperature and yielded alanine-aminocoumarin marked spheres having an internal Nile Red marker. The reaction mixture was dialyzed for four hours against DMF. Particles marked in this manner with the Nile Red and the alanine-aminocoumarin marker were refrigerated in the DMF until used.

By replacing the microspheres used in Example 1 by the Controlled Pore Glass, glass-based microparticles marked with alanine-aminocoumarin were also obtained. These glass-based microparticles exhibit a broad luminescence at about 600 nm due to the chemical constituency of the glass. Variations in the glass composition and the excitation wavelength will provide luminescence at different wavelengths.

EXAMPLE 3

In some applications, it is anticipated that the number of reactive sites on the microparticle available for attachment of the second marker compound will be the limiting factor. Although the technique taught in Examples 1 and 2 provides a compound in which each molecule of the second marker compound is directly attached to the substrate particle ("single loading"), it is also possible to achieve "multiple loading" of additional second marker molecules on the microparticle without increasing the number of attachment points on the microparticle surface. One such technique is to use a poly(amino acid) such as poly(lysine). Poly(lysine) is available commercially in chains having various average molecular weights. Two such commercially available chain lengths have average molecular weights of 4,000 and 10,000 molecular weight units. A 4,000 MW chain provides approximately fourteen reactive sites for attachment of the CFSE and a 10,000 MW chain provides approximately 34 such sites.

In a specific experiment, CFSE as in Example 1 was reacted with poly(lysine) (MW 4,000 in a first experiment and MW 10,000 in a second experiment) in ethyl acetate for three hours. This produced poly(lysine) chains loaded with the marker substrate. The loaded poly(lysine) chains were then attached to the same microparticles as in Example 1 by making a mixed anhydride with ethyl chloroformate and exposing the poly(lysine) chains to the microparticles. The particles were dialyzed against DMSO to remove unreacted compounds.

FIG. 1 shows a comparison of three systems of microparticles when exposed to otherwise identical esterase-containing environments, as described further below. In such an experiment, a single-loaded bead reacts with the environment and the emission intensity measured thereafter is essentially unchanged with time. When beads having multiple esterase reactive sites (4000 MW and 10000 MW) are used in the same environment, the poly(lysine) chains act in a fashion reminiscent of Christmas lights, and the emission intensity of the particles is observed to increase steadily with reaction time until each of the fluorescein molecules attached to the particle is "turned on" by reaction with the esterase. As is clearly seen from the data involving the multiple loadings, the poly(lysine) chains provide a steric hindrance to attack of the esterase, and the ultimate reaction of the second marker sites with the esterase is dependent upon time. By way of contrast, the single loaded second marker particles are almost instantly attacked by the esterase, and the emission intensity is essentially independent of time.

In this type of particle sensitivity enhancement, the enzyme substrate actually serves as a "blocking" group for the peptide coupling reaction that attaches the poly(lysine) chain to the particle. This permits peptide coupling to be performed without the traditional blocking (protecting) and de-blocking (de-protecting) chemistry that has been known in the past.

The increase of substrate loading also facilitates an increase in the amount of enzyme substrate delivered by the particle, permitting the use of smaller particles (recalling that surface area of a spherical particle drops with the square of the radius) or fewer larger particles, since substrate loading is directly related to surface area in the case of single loading. Additionally, the use of long marker-loaded chains attached to the particles may have further benefits, since it may be possible for the chains to span the membrane of certain cells and organisms.

Preparation of Enzymatic Assays

Salt solutions of esterase were obtained in liquid form from Sigma Chemical Co., and were stored under refrigeration. Carboxyfluorescein diacetate was obtained from Molecular Probes, Inc. Tris(hydroxymethyl)aminomethane ("THAM") was obtained from Sigma Chemical Co. Solutions were prepared using NANOPURE water obtained through water purification equipment commercially available through Barnstead Co.

Analysis of the Enzymatic Assays

Emission spectra were collected from the particles using a multichannel fluorimeter consisting of an argon-ion laser commercially sold by Coherent Co. for excitation at 488 nm, f/3 collection optics, a Spex CP200 spectrograph, and a Princeton Instruments charge coupled device ("CCD") detector. The CCD used an EEV 1152x298 one inch chip and was cooled by liquid nitrogen. Software developed in-house was used to control the instruments and analyze the data. The software was written in LABVIEW, a symbolic programming language available from national Instruments. The software was run on a MACINTOSH IIfx computer commercially available from Apple Computers of Cupertino, Calif. The samples were excited in the ultraviolet by a 250 W xenon arc lamp purchased from Oriel Corp.

Microorganisms Used

Rotifers of the species *Brachionis calycifiorus* were obtained from the Georgia Institute of Technology School of Biology. These were hatched from cysts overnight in a freshwater medium.

The Test

The organisms were allowed to feed on the particles prepared under the Example 1 protocol for 15 to 30 minutes. The organisms were then anaesthetized using tricaine-methyl-sulfonate. White light/fluorescence images were obtained with an inverted microscope (Olympus Model IMT-2)in an epifluorescence geometry using a 500 nm dichroic mirror obtained from Olympus and a Schott Glass 515 nm long-pass filter. Imaging was accomplished using a Javelin ⅔ inch CCD TV-rate camera in conjunction with a Perspectics video capture board and a MACINTOSH IIci computer. IPLAB software was used to control data acquisition and for data manipulation. The excitation was achieved by a Coherent argon-ion laser operating at 488 nm.

Test Results

The initial testing of the probe systems of the present invention has focused on the esterase and peptidase-related enzymes, because of their importance in biological systems.

Figure 2:
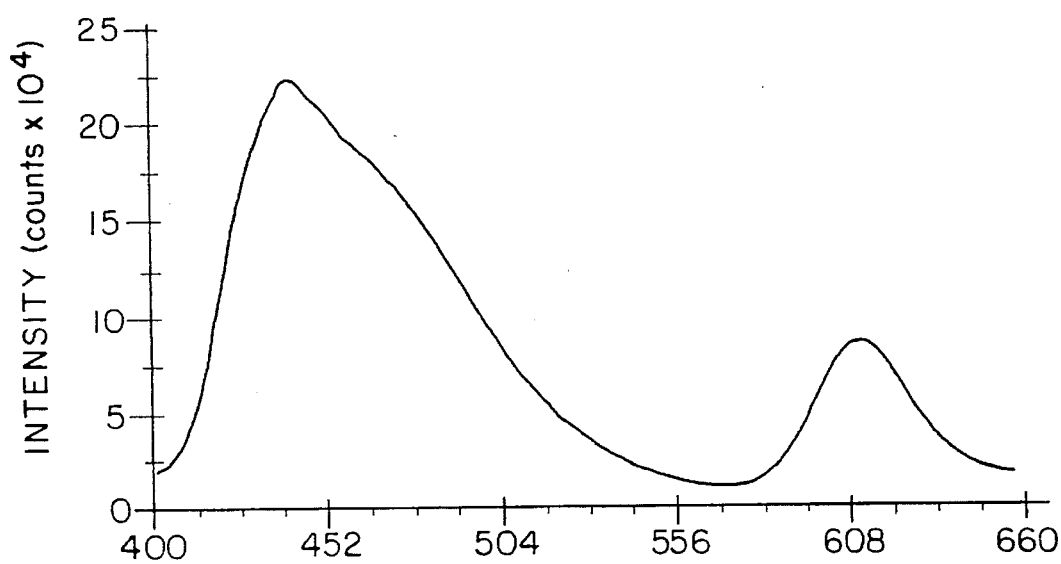
Figure 3:
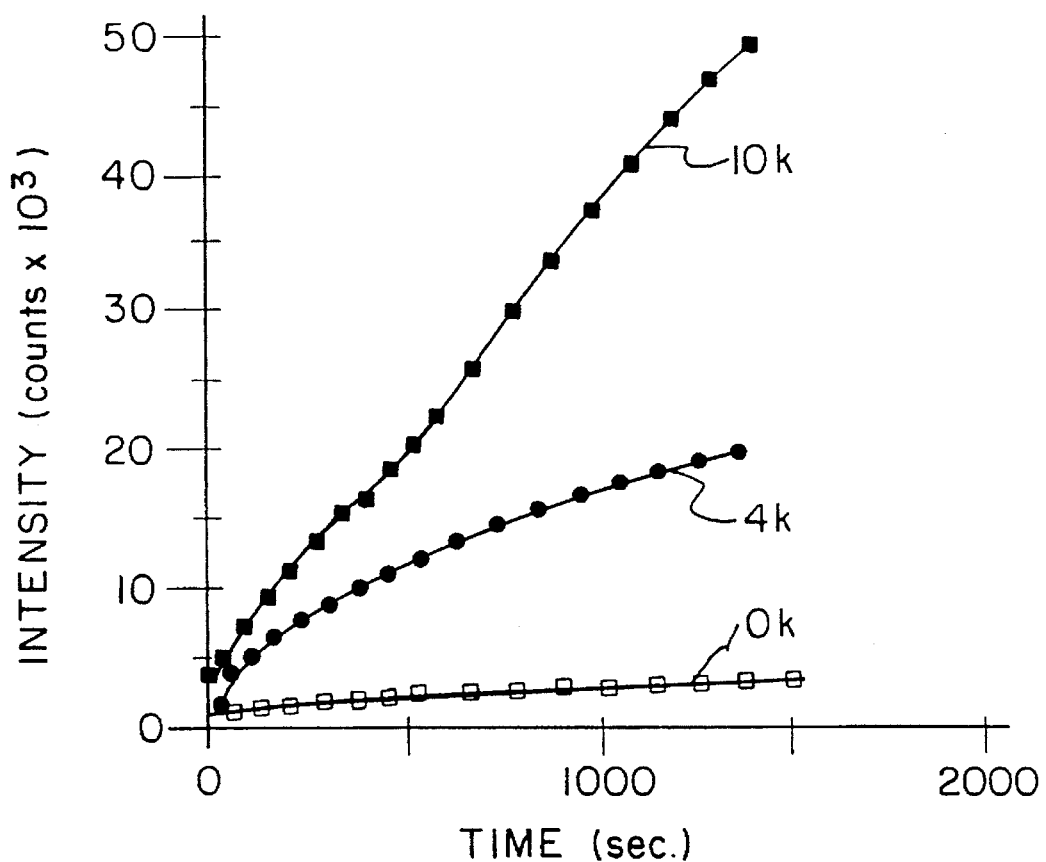
FIG. 3 shows a plot of relative emission intensity v. time for three different levels of second marker loading, as described in Example 3.

The esterase probe was prepared according to the method of Example 1. This esterase probe has the non-fluorescent second marker carboxyfluorescein diacetate covalently bound to the surface of a latex sphere that has been impregnated with the dye Nile Red, which acts as the first marker. When the acetoxymethyl esters are cleaved from the first marker by the target chemical esterase, the highly fluorescent fluorescein molecule is left attached to the particle. As is well known, fluorescein has an emission maximum near 520 nm when excited with 488 nm radiation. Nile Red has a well known emission intensity maximum at 605 nm when excited by radiation at 488 nm. Physical proximity of the first and second markers is such that radiation of the particle at 488 will result in discernable maxima near both 520 and 605 nm if the particle has had cleavage of the second marker by the esterase. Where no such cleavage has occurred, the particle will only exhibit emission at 605 nm. A typical example of the emission spectrum obtained from this protocol using the probe of Example 2 is shown as FIG. 2.

The synthesis of an aminopeptidase probe is illustrated by the protocol of Example 2, where AMC-acetic acid succinimidyl ester was linked through an amide linkage to the probe particle. Standard peptide synthesis then permitted covalent attachment of t-BOC-alanine to the 7-amino-4-methylcoumarin, although many other amino acids or peptide sequences could have been used, and the method of their use would be clear to persons having skill in the peptide synthesis. "Cleanup" of these reactions is accomplished by a quick dialysis, because the size of the attached probe particle eliminates any need for the chromatographic step that would otherwise be expected.

Because of the strong emission of Nile Red at 605 nm when excited at 488 nm, the experiments have focused on this dye as the first marker.

Further Uses of the Probe System

The probe system of the present invention having a chemically-isolated first marker and a spatially-linked second marker provides the researcher with a method for measuring chemical activity of a target chemical in an environment. The method comprising the steps of adding such a probe system to the selected environment and measuring the change in emission intensity ratio with time. In some these systems, the second marker is a chemical that emits at a characteristic wavelength after chemical cleavage by the target chemical, such as taught in the fluorescein diacetate example above. In certain other systems, the second marker will be a chemical that emits at the characteristic wavelength before chemical cleavage by the target chemical, but not after cleavage. The change in emission intensity ratio is measured through a conventional technique, such as digitized video fluorescent microscopy.

An Application to a Biological System

Measurement of in vivo enzymatic activity in an organism provides a technique for determining the level of stress in the organism. The aquaculture of larvae of shrimp or clams, which has extensive commercial importance in sections of the United States, has critical steps during which survival of the entire larval population could be at risk. Many environmental factors can be causative, among them poor water quality and overcrowding. If detected early, through the stress apparent in perhaps the most sensitive portion of the population, an early warning signal could be detected which could result in saving the greater portion of the population.

Larvae of Penaeus (shrimp) or Mercenaria (clams) are small, being in the range of about 0.5 to about 2 mm. When combined with trying to monitor conditions with instruments, the determination of the general health status of a larval population is difficult, if not impossible, using known techniques.

It is known in the prior art that stress, particularly environmental stress, causes a marked reduction in the in vivo activity of certain enzymes endogenous to the organism. This effect has been shown in a variety of aquatic invertebrates and fish, including rotifers, Daphnia, mysid shrimp, polychaetes, Artemia, fathead minnows and inland silversides. Once a researcher identifies a specific enzyme as one which exhibits this in vivo activity reduction under stress, a specific chemical probe system can be formulated to allow monitoring of stress in the organism. In such a probe, a microspherical particle as described in more detail above is prepared so that the particle is impregnated with a first marker compound that fluoresces when stimulated with light. This first marker compound, being internal to the microsphere, is chemically isolated from the environment being tested. Covalent bonding sites on the surface of the particle are used to attach a non-fluorescent enzyme substrate to the particle surface. The specific non-fluorescent substrate yields a highly fluorescent product after attack by the specific enzyme of interest.

In a biological system such as this, the second marker is a chemical that emits at a characteristic wavelength after chemical cleavage by the enzyme, such as in the fluorescein diacetate system taught above, or the second marker may be a chemical that emits at a characteristic wavelength only before chemical cleavage by the enzyme. In either case, the change in emission intensity ratio is measured through a conventional means, such as digitized video fluorescent microscopy.

While the best mode of practicing the present invention has been described in a fashion so as to provide an enabling disclosure, the actual scope of the invention is not to be measured by the foregoing specification, but is rather to be determined by the following claims.

What is claimed is:

1. A probe system for monitoring chemical activity of a target chemical in an environment, said probe system comprising:
   a) a carrier particle;
   b) a first marker, being a chemical that has a maximum emission intensity at a first wavelength, said first marker being chemically shielded from the environment; and
   c) a second marker, being a chemical that, when in a first state, has a maximum emission intensity at a second wavelength different from the first wavelength and which, in a second state, does not have a maximum emission intensity at the second wavelength, said second marker being convertible between said states through chemical reaction with the target chemical;
   wherein the first marker is impregnated within the carrier particle and the second marker is chemically bonded to the exterior surface of the carrier particle.

2. The probe system of claim 1 wherein the carrier particle comprises a glass material having a chemical composition such that the glass material is the first marker and the second marker is chemically bonded to the exterior surface of the carrier particle.

3. The probe system of claim 1 wherein the carrier particle comprises a polymeric material.

4. The probe system of claim 3 wherein the polymeric material is polystyrene.

5. The probe system of claim 1 wherein the carrier particle is a microsphere having a diameter in the range of 0.01 to about 50 microns in diameter.

6. The probe system of claim 1 wherein the second marker is in the second state prior to chemical reaction with the target chemical and is in the first state after chemical reaction with the target chemical.

7. The probe system of claim 1 wherein the second marker is in the first state prior to chemical reaction with the target chemical and is in the second state after chemical reaction with the target chemical.

8. The probe system of claim 1 wherein the second marker comprises a polymeric composition having a backbone structure with a plurality of molecules grafted onto the backbone structure along the length thereof, wherein said grafted molecules, when in a first state, have a maximum emission intensity at a second wavelength different from the first wavelength and which, in a second state, do not have a maximum emission intensity at the second wavelength, said grafted molecules being convertible between said states through chemical reaction with the target chemical.

9. The probe system of claim 8 wherein the backbone structure is a poly(amino acid).

10. The probe system of claim 9 wherein the poly(amino acid) is a poly(lysine) chain.

11. The probe system of claim 8 wherein the plurality of grafted molecules are molecules of 5,6 carboxyfluorescein diacetate.

12. A method for measuring chemical activity of a target chemical in an environment, said method comprising the steps of:
  a) adding a probe system to the environment, said probe system comprising
    1) a carrier particle;
    2) a first marker, being a chemical that emits in a first portion of the electromagnetic spectrum, said first marker being impregnated within the carrier particle and chemically shielded from the environment; and
    3) a second marker, being a chemical that changes its emission properties in a second portion of the electromagnetic spectrum after being chemically cleaved by the target chemical, said second marker being chemically bonded to the exterior surface of the carrier particle;
  wherein said probe system has a known initial emission intensity ratio, the emission intensity ratio being defined as the emission intensity of an emission maximum wavelength of the second marker divided by the emission intensity of an emission maximum wavelength of the first marker; and
  b) measuring and correlating the chemical activity of a target chemical to the change in emission intensity ratio with time.

13. The method of claim 12 wherein the second marker is a chemical that emits in said second portion of the electromagnetic spectrum after chemical cleavage by the target chemical.

14. The method of claim 12 wherein the second marker is fluorescein diacetate.

15. The method of claim 12 wherein the second marker is a chemical that emits in said second portion of the electromagnetic spectrum before chemical cleavage by the target chemical.

16. The method of claim 12 wherein the emission maximum wavelength of the first marker and the emission maximum wavelength of the second marker are separated by at least 50 nanometers.

17. The method of claim 12 wherein the change in emission intensity ratio is measured through digitized video fluorescent microscopy.

18. A method for measuring environmental stress in an aquatic organism, said method comprising the steps of:
  a) adding a probe system to an aquatic system containing a plurality of the aquatic organisms, said probe system comprising
    1) a carrier particle;
    2) a first marker, being a chemical that emits in a first portion of the electromagnetic spectrum, said first marker being impregnated within the carrier particle and chemically shielded from the environment; and
    3) a second marker, being a chemical that changes its emission properties in a second portion of the electromagnetic spectrum after being chemically cleaved by an enzyme present in the digestive tract of the aquatic organism, said second marker being chemically bonded to the exterior surface of the carrier particle;
  wherein said probe system has a known initial emission intensity ratio, the emission intensity ratio being defined as the emission intensity of an emission maximum wavelength of the second marker divided by the emission intensity of an emission maximum wavelength of the first marker;
  b) monitoring uptake of the probe system by the aquatic organism; and
  c) measuring the change in emission intensity ratio with time in the digestive tract of the aquatic organism.

19. The method of claim 18 wherein the second marker is a chemical that emits in said second portion of the electromagnetic spectrum after chemical cleavage by the enzyme.

20. The method of claim 18 wherein the second marker is a chemical that emits in said second portion of the electromagnetic spectrum before chemical cleavage by the enzyme.

21. The method of claim 18 wherein the emission maximum wavelength of the first marker and the emission maximum wavelength of the second marker are separated by at least 50 nanometers.

22. The method of claim 18 wherein the change in emission intensity ratio is measured through digitized video fluorescent microscopy.

* * * * *